US012569499B2

(12) United States Patent
Raman

(10) Patent No.: US 12,569,499 B2
(45) Date of Patent: Mar. 10, 2026

(54) INTRAVENOUS FORMULATIONS OF RK-33

(71) Applicant: NATSAR PHARMACEUTICALS, INC., Ellicott City, MD (US)

(72) Inventor: Venu Raman, Ellicott City, MD (US)

(73) Assignee: NATSAR PHARMACEUTICALS, INC., Ellicott City, MD (US)

( * ) Notice: Subject to any disclaimer, the term of this patent is extended or adjusted under 35 U.S.C. 154(b) by 0 days.

(21) Appl. No.: 17/822,922

(22) Filed: Aug. 29, 2022

(65) Prior Publication Data

US 2023/0077636 A1 Mar. 16, 2023

Related U.S. Application Data

(60) Provisional application No. 63/239,277, filed on Aug. 31, 2021.

(51) Int. Cl.

| | |
|---|---|
| ***A61K 31/5517*** | (2006.01) |
| ***A61K 9/50*** | (2006.01) |
| ***A61K 31/575*** | (2006.01) |
| ***A61K 31/79*** | (2006.01) |
| ***A61K 45/06*** | (2006.01) |

(52) U.S. Cl.

CPC ........ *A61K 31/5517* (2013.01); *A61K 9/5084* (2013.01); *A61K 31/575* (2013.01); *A61K 31/79* (2013.01); *A61K 45/06* (2013.01)

(58) Field of Classification Search

CPC .. A61K 31/5517; A61K 31/575; A61K 45/06; A61K 9/5084; A61K 31/79

See application file for complete search history.

(56) References Cited

U.S. PATENT DOCUMENTS

| | | | | |
|---|---|---|---|---|
| 4,801,455 A * | 1/1989 | List | A61K 9/113 | 514/939 |
| 5,145,684 A * | 9/1992 | Liversidge | A61K 49/0428 | 424/495 |
| 10,780,099 B2 | 9/2020 | Zhang et al. | | |
| 2005/0202092 A1 * | 9/2005 | Skantze | A61K 9/145 | 436/526 |
| 2011/0275588 A1 | 11/2011 | Hosmane et al. | | |
| 2013/0281440 A1 | 10/2013 | Raman et al. | | |
| 2021/0252153 A1 | 8/2021 | Mangraviti et al. | | |

FOREIGN PATENT DOCUMENTS

| | | | |
|---|---|---|---|
| EP | 3673897 | A1 | 7/2020 |
| EP | 3838265 | A1 | 6/2021 |
| WO | 2016/025741 | A1 | 2/2016 |
| WO | 2016/149273 | A1 | 9/2016 |

OTHER PUBLICATIONS

Guus Martinus Bol, et al, PLGA Nanoparticle Formulation of RK-33: An RNA Helicase Inhibitor Against DDX3, 76 Cancer Chemother. Pharmacol. 821 (Year: 2015).*

Aksenova et al., "Inhibition of the Dead Box RNA Helicase 3 prevents HIV-1 Tat and cocaine-induced neurotoxicity by targeting microglia activation," Journal of Neuroimmune Pharmacology 15:209-223 (2020).

Ali, "The DEAD-box protein family of RNA helicases: sentinels for a myriad of cellular functions with emerging roles in tumorigenesis", International Journal of Clinical Oncology 26(5):795-825 (2021).

Bol et al., "DOX3, a potential target for cancer treatment," Molecular Cancer 14(1):1-6 (2015).

Franco et al., "The Use of Poly(N-vinyl pyrrolidone) in the Delivery of Drugs: A Review," Polymers 12(5):1114 (2020).

Leuner and Dressman, "Improving drug solubility for oral delivery using solid dispersions", European journal of Pharmaceutics and Biopharmaceutics 50(1):47-60 (2000).

International Search Report and Written Opinion mailed Jan. 27, 2023 in International Application No. PCT/US2022/075585.

Botlagunta et al., "Oncogenic role of DDX3 in breast cancer biogenesis," Oncogene, 27(28):3912-3922 (2008).

Cruciat et al., "RNA helicase DDX3 is a regulatory subunit of casein kinase 1 in Wnt-β-catenin signaling," Science 339(6126):1436-1441 (2013).

Bogdanova, et al., "Micellization in sodium deoxycholate solutions," Colloid Journal 74(1):1-6 (2012).

Yang, et al., "RK-33 Is a Broad-Spectrum Antiviral Agent That Targets DEAD-Box RNA Helicase DDX3X," *Cells* 9(1):170 (2020).

Zhu, et al., "Preparation and in vitro evaluation of povidone-sodium cholate-phospholipid mixed micelles for the solubilization of poorly soluble drugs," *Archives of Pharmacal Research* 33(6): 911-917 (2010).

* cited by examiner

*Primary Examiner* — Sean M Basquill

(74) *Attorney, Agent, or Firm* — MEDLER FERRO WOODHOUSE & MILLS PLLC

(57) ABSTRACT

The present disclosure provides a liquid formulation comprising: (a) RK-33, (b) cholic acid or derivative thereof, (c) a water-soluble polyvinyl polymer, and (d) water. The disclosure also provides a method of making a liquid formulation comprising RK-33. The disclosure further provides a method of treating cancer in a subject in need thereof, the method comprising (a) diluting the formulation of the present disclosure to form a diluted formulation, and (b) intravenously administering to the subject the diluted formulation.

19 Claims, 3 Drawing Sheets

INTRAVENOUS FORMULATIONS OF RK-33

FIELD OF THE INVENTION

The present disclosure provides a liquid formulation comprising: (a) RK-33, (b) cholic acid or derivative thereof, (c) a water-soluble polyvinyl polymer, and (d) water. The disclosure also provides a method of making a liquid formulation comprising RK-33. The disclosure further provides a method of treating cancer in a subject in need thereof, the method comprising (a) diluting the formulation of the present disclosure to form a diluted formulation, and (b) intravenously administering to the subject the diluted formulation.

BACKGROUND

The DEAD-box helicase family member DDX3, which is involved in a number of cellular processes such as transcription, RNA splicing, mRNA export, and translation initiation, is known to be linked to the progression of cancer when overexpressed. Recent advancements in cancer research and treatment provide novel fused diimidazodiazepine compounds that bind to and inhibit DDX3, which results in the activation of cell death pathways, inhibition of the Wnt-signaling pathway, and abrogation of non-homologous end-joining activity. RK-33 is a member of the class of fused diimidazodiazepine compounds that produced effective results in inhibiting the growth of tumor cells in multiple cancers including sarcoma, breast, prostate, colorectal, lung, and medulloblastoma without affecting healthy and "normal" cells.

A common method of delivering chemotherapy or anti-cancer drugs to a cancer patient includes administering the drug through a needle or tube inserted directly into a vein. There are several advantages to intravenous administration such as increased drug availability with minimal delay, the ability to control rate of administration and the direct administration of drugs that are otherwise poorly absorbed by the gastrointestinal tract. However, due to the difficulty in formulation RK-33, no intravenous formulation was previously known.

SUMMARY OF THE INVENTION

The present disclosure is directed to a liquid formulation comprising, (a) RK-33, (b) cholic acid or derivative thereof, (c) a water-soluble polyvinyl polymer, and (d) water.

In some embodiments, the formulation comprises about 1 mg/mL to about 30 mg/mL of RK-33. In some embodiments, the formulation comprises about 15 mg/mL to about 25 mg/mL of RK-33.

In some embodiments, the cholic acid or derivative thereof is a sodium or potassium salt of cholic acid or derivative thereof. In some embodiments, the cholic acid or derivative thereof is deoxycholate. In some embodiments, the cholic acid or derivative thereof is sodium deoxycholate. In some embodiments, the formulation is about 0.05% w/w to about 1.0% w/w of the cholic acid or derivative thereof. In some embodiments, the formulation is about 0.2% w/w to about 0.6% w/w of the cholic acid or derivative thereof.

In some embodiments, the water-soluble polyvinyl polymer is polyvinylpyrrolidone (PVP), polyvinyl alcohol (PVOH), polyvinyl alcohol-polyethylene glycol copolymer, or polyvinylpyrrolidone-polyvinyl acetate (PVP-VA). In some embodiments, the polyvinylpyrrolidone has an average molecular weight of about 1000 kDa to about 20,000 Da.

In some embodiments, the polyvinylpyrrolidone has an average molecular weight of about 4,000 to about 6,000 Da.

In some embodiments, the formulation is an aqueous suspension. In some embodiments, particles in the suspension have a D50 particle size of about 0.05 μm to about 0.5 μm. In some embodiments, particles in the suspension have a D50 particle size of about 0.10 μm to about 0.2 μm. In some embodiments, particles in the suspension have a D90 particle size of about 0.1 μm to about 0.5 μm. In some embodiments, particles in the suspension have a D90 particle size of about 0.15 μm to about 0.3 μm. In some embodiments, particles in the suspension have an average particle size of about 0.05 μm to about 0.5 μm. In some embodiments, the particles in the suspension have an average particle size of about 0.10 μm to about 0.2 μm. In some embodiments, the average particle size in the suspension does not change by more than 25% after storage at room temperature for two weeks.

In some embodiments, the formulation is sterile. In some embodiments, the formulation is pharmaceutically acceptable. In some embodiments, the formulation is isotonic. In some embodiments, the formulation further comprises another chemotherapeutic agent.

In some embodiments, the disclosure is directed to a liquid formulation comprising, (a) about 10% to about 25% (wt/wt) RK-33, (b) about 0.1% to about 1.0% (wt/wt) sodium deoxycholate; (c) about 1% to about 10% PVP; and (d) water.

In some embodiments, the disclosure provides a method of making a liquid formulation comprising RK-33, the method comprising: (a) combining the RK-33, cholic acid or derivative thereof, a water-soluble polyvinyl polymer, and water to form a mixture, and (b) milling the mixture, wherein the method results in an aqueous suspension comprising particles.

In some embodiments, the milling is performed using a vibratory ball mill. In some embodiments, the formulation is milled at about 1,000 RPM to about 10,000 RPM. In some embodiments, the formulation is milled at about 2,000 RPM to about 4,000 RPM. In some embodiments, the formulation is milled for at least 10 minutes. In some embodiments, the formulation is milled for about 5 minutes to about 5 hours. In some embodiments, the formulation is milled for about 20 minutes to about 60 minutes.

In some embodiments, the milling occurs until the particles in the suspension have a D50 particle size of about 0.05 μm to about 0.5 μm. In some embodiments, the milling occurs until the particles in the suspension have a D50 particle size of about 0.10 μm to about 0.2 μm. In some embodiments, the milling occurs until the particles in the suspension have a D90 particle size of about 0.1 μm to about 0.5 μm. In some embodiments, the milling occurs until the particles in the suspension have a D90 particle size of about 0.15 μm to about 0.3 μm. In some embodiments, the milling occurs until the particles in the suspension have an average particle size of about 0.05 μm to about 0.5 am. In some embodiments, the milling occurs until the particles in the suspension have an average particle size of about 0.10 μm to about 0.2 am.

In some embodiments, the disclosure is directed to a method of treating a cancer in a subject, the method comprising (a) diluting the formulation as described in the present disclosure to form a diluted formulation, and (b) intravenously administering to the subject the diluted formulation.

In some embodiments, the method further comprises subjecting the subject to focused radiation. In some embodiments, the focused radiation is stereotactic ablative radiotherapy (SABR). In some embodiments, the formulation is administered to the subject about 10 minutes to about 1 week before the focused radiation. In some embodiments, the formulation is administered one to ten times before the focused radiation. In some embodiments, the method further comprises administering a second chemotherapeutic agent. In some embodiments, the method is repeated two to 20 times. In some embodiments, the administering continues until the symptoms associated with the cancer are substantially eliminated. In some embodiments, the cancer is lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, chronic or acute leukemia, lymphocytic lymphomas, cancer of the bladder, cancer of the kidney, renal cell carcinoma, neoplasms of the central nervous system (CNS), neuroectodermal cancer, spinal axis tumors, glioma, meningioma, and pituitary adenoma.

In some embodiments, the disclosure is directed to a kit comprising the formulation of as described in the present disclosure and a packaging suitable for storing the formulation. In some embodiments, the packaging is a vial, a pre-filled syringe or an IV bag.

DETAILED DESCRIPTION OF THE INVENTION

Figure 1A:
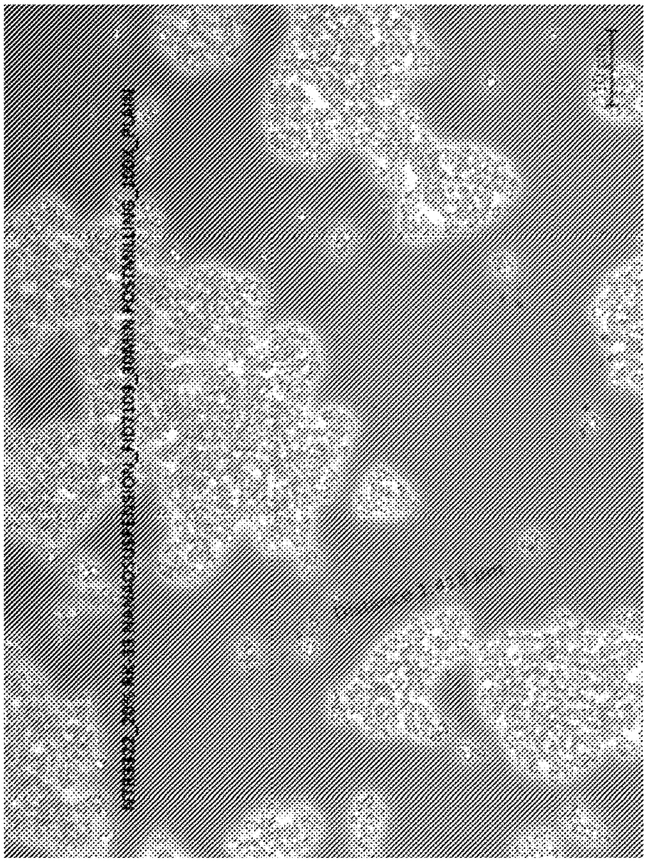
FIG. 1A is a photo of particle aggregation of Formulation T41 observed under the microscope.

The present disclosure relates to a liquid formulation comprising the compound RK-33. Previous attempts to deliver RK-33 through intravenous administration were challenging due to issues with intrinsic solubility of the compound in solvents. In some embodiments, the present disclosure provides a liquid formulation that is stable, both chemically and physically. In some embodiments, the disclosure provides a stable aqueous suspension that is suitable for dilution and subsequent intravenous administration. In some embodiments, the disclosure provides a liquid formulation comprising, (a) RK-33 as represented by Formula I Formula I

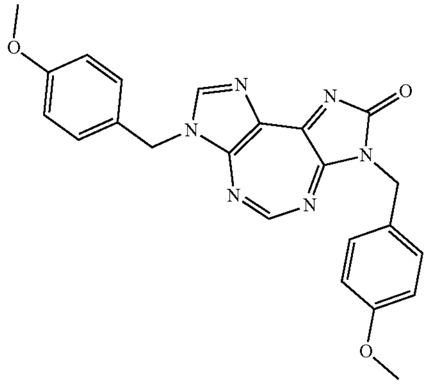
;

(b) cholic acid or derivative thereof, (c) a water-soluble polyvinyl polymer, and (d) water.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability, depending on the situation.

The use of the term "or" in the claims is used to mean "and/or", unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps. It is contemplated that any embodiment discussed in this specification can be implemented with respect to any formulation, methods, and/or kits of the present disclosure.

The use of the term "for example" and its corresponding abbreviation "e.g.," (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

The present disclosure provides liquid pharmaceutical formulations comprising RK-33. RK-33 is also described in WO 2016/0149273, incorporated by references herein in its entirety, and is represented by Formula I:

Formula I

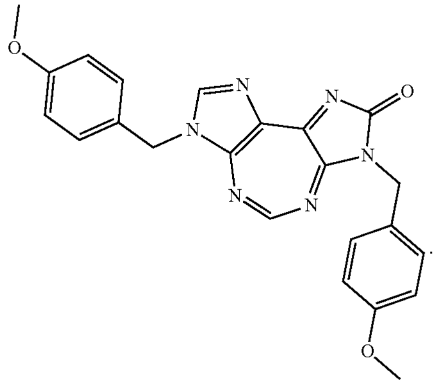

As used herein, the term RK-33 includes its salts and solvates thereof. It was previously shown that targeting DDX3 by RK-33 promotes cell death. See, e.g., Oncogene, 27(28): 3912-3922 (2008), incorporated by reference herein in its entirety. DDX3 is known to be overexpressed in breast and lung cancers. The role of DDX3 in breast and lung cancers can in part be explained by its involvement in Wnt signaling. See, e.g., Science 2013; 339(6126): 1436-1441, incorporated by reference herein in its entirety. A majority of colorectal cancers are driven by mutations in the Wnt-signaling pathway, and it was previously shown that DDX3 is overexpressed in 39% of colorectal cancers. See, e.g., WO 2016/0149273. Applicant previously demonstrated that inhibition of DDX3 results in reduced Wnt signaling and a G1 arrest, making DDX3 an attractive therapeutic target in these cancers. Thus, in some embodiments, the formulations described herein are useful for the inhibition of DDX3. In some embodiments, the formulations described herein can be used to reduce Wnt signaling and/or GI arrest.

Various concentrations of RK-33 can be present in the formulations described herein. In some embodiments, the formulation is diluted in a separate solution, e.g., an isotonic solution, prior to use. For example, in some embodiments, the formulation comprising RK-33 is diluted into an isotonic solution such as a saline solution, prior to administration to a subject. In some embodiments, the formulation comprises about 1 mg/mL to about 30 mg/mL, about 2 mg/mL to about 28 mg/mL, about 3 mg/mL to about 26 mg/mL, about 4 mg/mL to about 27 mg/mL, about 5 mg/mL to about 25 mg/mL, about 6 mg/mL to about 23 mg/mL, about 7 mg/mL to about 22 mg/mL, about 8 mg/mL to about 21 mg/mL, or about 10 mg/mL to about 20 mg/mL RK-33. In some embodiments, the formulation comprises about 10 mg/mL to about 30 mg/mL, about 15 mg/mL to about 25 mg/mL, or about 18 mg/mL to about 22 mg/mL RK-33. In some embodiments, the formulation comprises about 20 mg/mL RK-33. The disclosure provides for formulations suitable for liquid formulations comprising RK-33, wherein the RK-33 does not precipitate, and wherein aggregation of any RK-33 particles is minimized. The skilled artisan will appreciate that the concentrations described here can refer to formulations suitable for dilution, and thus it is within the scope and intent of the disclosure to encompass more diluted concentrations of RK-33.

In some embodiments, other active agents similar to RK-33 can be used in the formulations described herein. E.g., in some embodiments, the RK-33 can be replaced by any active agent described in WO 2016/149273, incorporated by reference in its entirety. In some embodiments, the disclosure provides formulations comprising a compound of Formula (II):

(II)

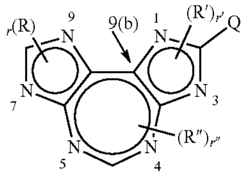

or pharmaceutically acceptable salts and prodrugs thereof, wherein:

- R, R', and R are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —$C(O)R^3$; —$C(S)R^3$; —$S(O)R^3$; —$S(O)_2R^3$; —$C(O)NR^4R^5$; —$C(S)NR^3R^4$; —$C(X)YR^5R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens;
- R, R', and R can also form a ring with one or more C, S, O, N atoms such that, for example, R and R' together include:

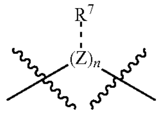

- $R^7$ is a hydrogen; hydroxyl; substituted or unsubstituted cyclic and acyclic alkyl group, group, alkenyl group, alkynyl group, aryl group, group, alkylaryl group, aryalkyl group, heteroaryl group, heterocycloalkyl group; —C(O)alkyl; —C(O)alkenyl; —C(O)alkynyl; —C(O)aryl; —C(O)benzyl; —$C(O)NR^3R^4$; —C(S)alkyl; —C(S)alkenyl; —C(S)alkynyl; —C(S)aryl; —C(S)benzyl; —$C(S)NR^3R^4$; —$C(X)YR^1R^2$; wherein
- Q is O, NH, or S;
- X is O, N, or S;
- Y is O, $CH_2$, NH, or S;
- Z is CH, N, P, or C; is a single bond or double bond; wherein if is a double bond, $R^2$ or $R^7$ is independently O, S, or NH; n is 1, 2, 3, or 4; and r, r', and r" are each independently an integer from 1 to about 3.

In some embodiments, R is substituted benzyl. In some embodiments, R' is substituted benzyl. In some embodiments, R" is substituted phenyl. In some embodiments, R and R' are each a substituted benzyl. In some embodiments, R is cyclic and acyclic alkyl; aryl; heteroalkyl; or heteroaryl. In some embodiments, R' is cyclic and acyclic alkyl; aryl; heteroalkyl; or heteroaryl. In some embodiments, the cyclic and acyclic alkyl; aryl; heteroalkyl; heteroaryl are substituted. In some embodiments, the cyclic and acyclic alkyl aryl; heteroalkyl; and heteroaryl are substituted. In some embodiments, R" is hydrogen, R is substituted benzyl, and R' is substituted benzyl. In some embodiments, R" is hydrogen, R is p-methoxybenzyl, and R' is p-methoxy-benzyl. In some embodiments, R" is hydrogen, R is p-methoxybenzyl, and R' is p-methoxy-benzyl. In some embodiments, R is covalently bonded to the 7-position. In some embodiments, R' is covalently bonded to the 3-position. In some embodiments, wherein R" is substituted phenyl. In some embodiments, the substituted phenyl is p-methoxyphenyl. In some embodiments, R is hydrogen, R' is p-methoxybenzyl and R" is p-methoxy-phenyl. In some embodiments, R is hydrogen, R' is p-methoxybenzyl and R" is p-methoxy-phenyl and R' is substituted on the 3 position, R" is substituted on the 9(b) position and Q is oxygen.

Thus, in some embodiments, the disclosure provides a liquid formulation comprising, (a) a compound represented by Formula II (II)

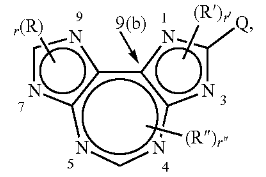

(b) cholic acid or derivative thereof, (c) a water-soluble polyvinyl polymer, and (d) water.

In another embodiment, the disclosure provides formulations comprising a compound of Formula (III):

(III)

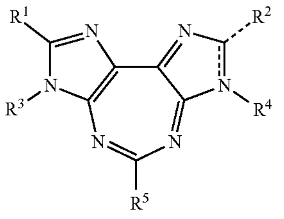

or pharmaceutically acceptable salts and prodrugs thereof, wherein $R^1$, $R^2$, $R^3$, $R^4$, and $R^6$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S(O)$_2R^3$; —C(O)$NR^4R^5$; —C(S)$NR^3R^4$; —C(X)$YR^5R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens; $R^1$ and $R^3$ or $R^2$ and $R^4$ can also form a ring with one or more C, S, O, N atoms such that $R^1$ and $R^3$ or $R^2$ and $R^4$ together include

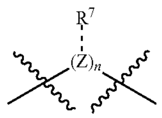

$R^7$ is a hydrogen; hydroxyl; substituted and unsubstituted: cyclic and acyclic alkyl group, group, alkenyl group, alkynyl group, aryl group, aryloxy group, alkylaryl group, arylalkyl group, heteroaryl group, heterocycloalkyl group; —C(O)alkyl; —C(O)alkenyl; —C(O)alkynyl; —C(O)aryl; —C(O)benzyl; —C(O)$NR^3R^4$; —C(S)alkyl; —C(S)alkenyl; —C(S)alkynyl; —C(S)aryl; —C(S)benzyl; —C(S)$NR^3R^4$; —C(X)$YR^1R^2$; wherein X is O, N, or S; Y is O, $CH_2$, NH, or S; Z is CH, N, P, or C; is a single bond or double bond; wherein if is a double bond, $R^2$ or $R^7$ is independently O, S, or NH; and n is 1, 2, 3, or 4.

In certain illustrative embodiments, $R^1$, $R^2$, $R^3$, $R^4$, and $R^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalkyl, alkyloxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

In another embodiment, the disclosure provides formulations comprising a compound of Formula (IV)

(IV)

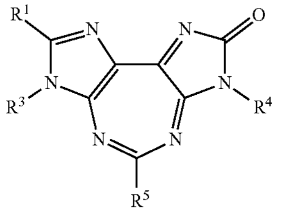

or pharmaceutically acceptable salts and prodrugs thereof, wherein $R^1$, $R^3$, $R^4$, and $R^5$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S(O)$_2R^3$; —C(O)$NR^4R^5$; —C(S)$NR^3R^4$; —C(X)$YR^5R^6$; -β-D-ribosyl; -α-D-ribosyl; -β-L-ribosyl; -α-L-ribosyl; 2'-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens;

$R^1$ and $R^3$ can also form a ring with one or more C, S, O, N atoms such that $R^1$ and $R^3$ together include

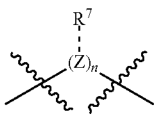

$R^7$ is a hydrogen; hydroxyl; substituted and unsubstituted: cyclic and acyclic alkyl group, group, alkenyl group, alkynyl group, aryl group, aryloxy group, alkylaryl group, arylalkyl group, heteroaryl group, heterocycloalkyl group; —C(O)alkyl; —C(O)alkenyl; —C(O)alkynyl; —C(O)aryl; —C(O)benzyl; —C(O)$NR^3R^4$; —C(S)alkyl; —C(S)alkenyl; —C(S)alkynyl; —C(S)aryl; —C(S)benzyl; —C(S)$NR^3R^4$; —C(X)$YR^1R^2$; wherein X is O, N, or S;

Y is O, $CH_2$, NH, or S;

Z is CH, N, P, or C; is a single bond or double bond; wherein if is a double bond, $R^2$ or $R^7$ is independently O, S, or NH; and n is 1, 2, 3, or 4.

In certain illustrative embodiments, $R^1$, $R^3$, $R^4$, and $R^5$ are not all hydrogen. In certain illustrative embodiments, $R^1$, R, $R^4$, and $R^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalkyl, alkyloxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

In another embodiment, the disclosure provides formulations comprising a compound of Formula (V):

(V)

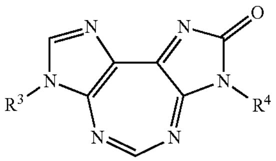

or pharmaceutically acceptable salts and prodrugs thereof, wherein $R^3$ and $R^4$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S$(O)_2R^3$; —C(O)$NR^4R^5$; —C(S)$NR^3R^4$; —C(X)$YR^5R^6$; -β-D-ribosyl; -α-D-ribosyl; -β-L-ribosyl; -α-L-ribosyl; T-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens.

In certain illustrative embodiments, $R^3$ and $R^4$ are both not hydrogen. In certain illustrative embodiments, R and $R^4$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalkyl, alkyloxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

In another embodiment, the disclosure provides formulations for treating or comprising a compound of Formula (VI):

(VI)

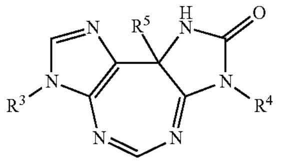

or pharmaceutically acceptable salts and prodrugs thereof, wherein $R^3$, $R^4$, and $R^5$ are each independently a hydrogen; hydroxyl; substituted or unsubstituted: cyclic and acyclic alkyl group, cyclic and acyclic alkenyl group, cyclic and acyclic alkynyl group, aryl group, alkylaryl group, arylalkyl group, benzyl group, cyclic and acyclic heteroalkyl group, heteroaryl group; —C(O)$R^3$; —C(S)$R^3$; —S(O)$R^3$; —S$(O)_2R^3$; —C(O)$NR^4R^5$; —C(S)$NR^3R^4$; —C(X)$YR^5R^6$; -β-D-ribosyl; -α-D-ribosyl; -β-L-ribosyl; -α-L-ribosyl; T-deoxy-β-D-ribosyl; 2'-deoxy-β-L-ribosyl; 2'-deoxy-α-D-ribosyl; 2'-deoxy-α-L-ribosyl; and ribose or deoxyribose sugars substituted with one or more halogens. In certain illustrative embodiments, $R^3$, $R^4$, and $R^5$ are not each hydrogen. In certain illustrative embodiments, $R^3$, $R^4$, and $R^5$ are each independently are a substituted benzyl, alkyl, aryl, cycloalkyl, heteroaryl, or heterocycloalkyl with one or more substituents, such as, but not limited to, —H, —F, —Cl, —Br, —I, —OH, azido, —SH, alkyl, aryl, heteroalkyl, alkyloxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl.

The disclosure provides for a liquid formulation comprising a cholic acid or derivative thereof. The phrase "cholic acid or derivative thereof," as used herein, refers to a class of compounds with the general structure:

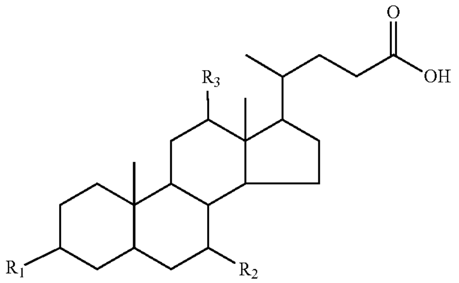

or stereoisomers, salts, or solvates thereof, wherein $R_1$, $R_2$ and $R_3$ are independently hydrogen, hydroxy, oxo, $C_1$-$C_6$ alkyl, $C_1$-$C_6$ alkylether, $C_1$-$C_6$ alkylester, $C_1$-$C_6$ alkylamino or $C_1$-$C_6$ alkylamido. In some embodiments, $R_1$, $R_2$ and $R_3$ are independently hydrogen, hydroxy, oxo, or $C_1$-$C_6$ alkyl. In some embodiments, $R_1$, $R_3$ are independently hydrogen, hydroxy, oxo, or $C_1$-$C_6$ alkyl, and $R_2$ is hydrogen. In some embodiments. $R_1$ is hydroxy. In some embodiments, $R_2$ is hydrogen. In some embodiments, $R_3$ is hydroxy.

In some embodiments, the phrase "cholic acid or derivative thereof," refers to a class of compounds with the general structure:

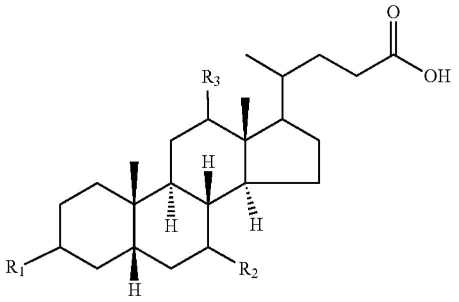

salts, or solvates thereof, wherein $R_1$, $R_2$ and $R_3$ are independently hydrogen, hydroxy, oxo, $C_1$-$C_6$alkyl, $C_1$-$C_6$ alkylether, $C_1$-$C_6$ alkylester, $C_1$-$C_6$ alkylamino or $C_1$-$C_6$ alkylamido. In some embodiments, $R_1$, $R_2$ and $R_3$ are independently hydrogen, hydroxy, oxo, or $C_1$-$C_6$ alkyl. In some embodiments, $R_1$, $R_3$ are independently hydrogen, hydroxy, oxo, or $C_1$-$C_6$ alkyl, and $R_2$ is hydrogen. In some embodiments, $R_1$ is hydroxy. In some embodiments, $R_2$ is hydrogen. In some embodiments, $R_3$ is hydroxy. The stereocenters not specified above can include any stereoisomers.

In some embodiments, the phrase "cholic acid or derivative thereof" can include deoxycholic acid, 3α,7α,12β-trihydroxy-5b-cholanoic acid, 3-oxo-7α-hydroxy-5β-cholanoic acid, 5β-cholanic acid, 3α-hydroxy-7-keto cholanic acid, 3β,12α-dihydroxy-5β-cholanoic acid, 3α,7α-dihydroxy-12-oxo-5β-cholanic acid, 3α,12β-dihydroxy-5β-cholanoic acid, 5α-cholanic, 3-oxo-12α-hydroxy-5β-cholanoic acid, 3-oxo-5β-cholanoic acid, or 3β,12α-dihydroxy-5β-cholanoic acid.

In some embodiments, the "cholic acid or derivative thereof" is deoxycholate as represented by:

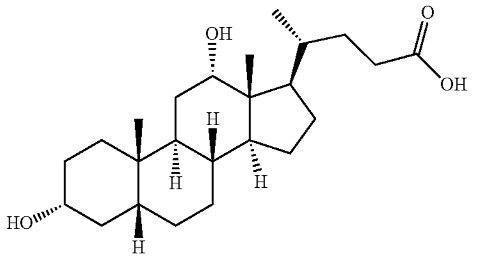

In some embodiments, the deoxycholate is a salt of deoxycholate, e.g., a potassium or sodium salt of deoxycholate. In some embodiments, the phrase "cholic acid or derivative thereof" is sodium deoxycholate.

Various concentrations of the cholic acid or derivative thereof can be used according to the present invention. In some embodiments, the formulation is about 0.01% w/w to about 2.0% w/w, about 0.05% w/w to about 1.0% w/w, or about 0.1% w/w to about 0.8% w/w cholic acid or derivative thereof. In some embodiments, the formulation is about 0.2% w/w to about 0.6% w/w cholic acid or derivative thereof. In some embodiments, the formulation is about 0.01% w/w to about 2.0% w/w, about 0.05% w/w to about 1.0% w/w, or about 0.1% w/w to about 0.8% w/w deoxycholate. In some embodiments, the formulation is about 0.2% w/w to about 0.6% w/w deoxycholate. In some embodiments, the formulation is about 0.01% w/w to about 2.0% w/w, about 0.05% w/w to about 1.0% w/w, or about 0.1% w/w to about 0.8% w/w sodium deoxycholate. In some embodiments, the formulation is about 0.2% w/w to about 0.6% w/w sodium deoxycholate.

The disclosure provides formulations comprising a water-soluble polyvinyl polymer. The term polyvinyl polymer refers to a polymer of the general formula:

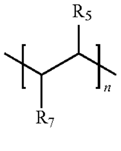

wherein $R_5$ and $R_6$ are independently hydrogen, hydroxy, $C_1$-$C_6$ alkyl, heterocycle, heterocycle alkyl, heteroaryl, or heteroaryl alkyl, wherein the $C_1$-$C_6$ alkyl, heterocycle, heterocycle alkyl, heteroaryl, or heteroaryl alkyl is optionally substituted with $C_1$-$C_6$ alkyl, hydroxy or oxo. In some embodiments, $R_5$ is hydrogen, and $R_6$ is hydrogen or hydroxy. In some embodiments, $R_6$ is hydrogen, and $R_5$ is hydroxy, $C_1$-$C_6$ alkyl, heterocycle, heterocycle alkyl, heteroaryl, or heteroaryl alkyl, wherein the $C_1$-$C_6$ alkyl, heterocycle, heterocycle alkyl, heteroaryl, or heteroaryl alkyl is optionally substituted with $C_1$-$C_6$ alkyl, hydroxy or oxo. In some embodiments, $R_5$ is hydrogen, and $R_6$ is hydroxy, $C_1$-$C_6$ alkyl, heterocycle, heterocycle alkyl, heteroaryl, or heteroaryl alkyl, wherein the $C_1$-$C_6$ alkyl, heterocycle, heterocycle alkyl, heteroaryl, or heteroaryl alkyl is optionally substituted with $C_1$-$C_6$ alkyl, hydroxy or oxo. In some embodiments, $R_5$ or $R_6$ is heterocycle, heterocycle alkyl, heteroaryl, or heteroaryl alkyl, optionally substituted with $C_1$-$C_6$ alkyl, hydroxy or oxo. In some embodiments, $R_6$ is hydrogen, and $R_5$ is heterocycle, heterocycle alkyl, heteroaryl, or heteroaryl alkyl, optionally substituted with $C_1$-$C_6$ alkyl, hydroxy or oxo. In some embodiments, the polyvinyl polymer is pharmaceutically acceptable.

One of skill in the art will appreciate that not all subunits of the polymer may be identical, and that substitutions on $R_5$ and/or $R_6$ may vary on each subunit. One of skill in the art can appreciate that in some instances, the terminal ends of the polymer can be modified without changing the overall properties of the polymer and are known to the skilled artisan. Thus, it is understood that terminal modifications of a polyvinyl polymer fall within the scope of the term polyvinyl polymer. In some embodiments, the terminal ends comprise a hydrogen and/or ahydroxy.

In some embodiments, the heterocycle, heterocycle alkyl, heteroaryl, or heteroaryl alkyl is optionally substituted with hydroxy or oxo. In some embodiments, the heterocycle, heterocycle alkyl, heteroaryl, or heteroaryl alkyl is optionally substituted with oxo. In some embodiments, the heterocycle, heterocycle alkyl, heteroaryl, or heteroaryl alkyl is selected from the group consisting of pyrrolidone, pyrrolidone, pyrrole, oxolane, oxolanone, furane or furanone. In some embodiments, the heterocycle, heterocycle alkyl, heteroaryl, or heteroaryl alkyl is 2-pyrollidone, 3-pyrollidone, methylpyrrolidone, ethylpyrrolidone, 2-oxolanone, 3-oxolanone, 2-furanone, 3-funanone. In some embodiments, the heterocycle is 2-pyrollidone or 3-pyrollidone.

In some embodiments, the water-soluble polyvinyl polymer is polyvinylpyrrolidone (PVP), polyvinylalcohol (PVOH), polyvinyl alcohol-polyethylene glycol copolymer, or polyvinylpyrrolidone-polyvinylacetate (PVP-VA).

In some embodiments, the water-soluble polyvinyl polymer is a polyvinyl alcohol. In some embodiments, the water-soluble polyvinyl polymer is a polyvinyl pyrrolidone of the general formula

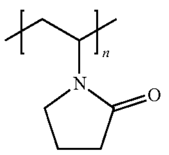

In some embodiments, n is about 10-15,000, 12 to 1,000, 12 to about 500, 15 to about 100, or about 18 to about 30.

In some embodiments, n is about 18 to about 27, about 63 to about 99, about 396 to about 485, or about 8,900 to about 13,500.

In some embodiments, the polyvinyl polymer has a molecular weight of about 1000 Da to about 30,000 Da, about 1000 Da to about 20,000 Da, about 1,500 Da to about 6 kDa, about 1,800 Da to about 11 kDa, about 2,000 Da to about 5,000 Da or about 4,000 Da to about 6,000 Da. In some embodiments, the polyvinyl polymer has a molecular weight of about 3000 Da to about 3,000 Da, about 7,000 kDa, about 11,000 Da, about 44 kDa to about 54 kDa, or about 1,000 kDa to about 1,500 kDa. In some embodiments the water-soluble polyvinyl polymer is a polyvinyl pyrrolidone, selected from Povidone K90, Povidone K30, Povidone K25, Povidone K17, Povidone K15, or Povidone K12. In some embodiments, the water-soluble polyvinyl polymer is Povidone K30, Povidone K25, Povidone K17, Povidone K15, or Povidone K12. In some embodiments, the water-soluble polyvinyl polymer is Povidone K17, Povidone K15, or Povidone K12. In some embodiments, the water-soluble polyvinyl polymer is Povidone K12.

The polyvinyl polymer as used herein is soluble in water, i.e., is water soluble. In some embodiments, the polyvinyl polymer is soluble at greater than about 30 mg/mL, greater than about 50 mg/mL, greater than about 60 mg/mL, greater than about 70 mg/mL, greater than about 80 mg/mL, greater than about 90 mg/mL, or greater than about 100 mg/mL. Solubility can be measured at standard conditions, e.g., room temperature and 1 atmosphere pressure.

In some embodiments, the formulation is an aqueous suspension. The term aqueous suspension refers to a suspension that is greater than 50%, greater than 60%, or greater than 70% water in which one or more particles is suspended. In some embodiments, the particles are suspended in the aqueous suspension for an extended period of time without visible precipitation under standard temperatures and pressure. For example, in some embodiments, the particles are suspended in the aqueous suspension for an extended period of time, e.g., for greater than 1 week, greater than 2 weeks, greater than 3 weeks, greater than 4 weeks, greater than 1 month, greater than 3 months, greater than 6 months or greater than 1 year, without visible precipitation.

In some embodiments, the formulation does not comprise significant aggregation of particles of RK-33. The term "significant aggregation" refers formulations with less than 5, less than 4, less than 3, less than 2, or less than 1 aggregates (on average) in a field of vision of an optical microscope at 1000×. In some embodiments, the particles are suspended in the aqueous suspension for an extended period of time, e.g., for greater than 1 week, greater than 2 weeks, greater than 3 weeks, greater than 4 weeks, greater than 1 month, greater than 3 months, greater than 6 months or greater than 1 year, with no significant aggregation as verified using an optical microscope at 1000×.

In some embodiments, the particles in the suspension comprise RK-33. The disclosure provides a formulation in which RK-33 is in a stable aqueous suspension, that can be stored for an extended period of time while the particles comprising RK-33 remain in the suspension. In some embodiments, the stable RK-33 formulations can then be diluted prior to administration to a subject.

In some embodiments, the RK-33 can be milled and sieved to achieve a particle size sufficient to remain in the aqueous suspension. Methods of determining particle size are known in the art, and can include, e.g., sieve analysis, dynamic light scattering, laser diffraction, static image analysis, or dynamic image analysis. As used herein, the term "particle size" is based on the particle size, and not particle volume. In some embodiments, the particle size measurements are determined using laser diffraction apparatus. For example, in some embodiments, the particle size distribution (PSD) analyses of RK-33 suspension samples can be conduct using a laser diffraction apparatus, e.g., a Horiba LA960 laser diffraction apparatus. Procedures for measuring particle size will be dependent on the specific formulation and the particle size apparatus being used. In some embodiments, samples for particle size determination can be prepared by diluting the formulations described herein in deionized water, e.g., a 1:1 to about a 1:20 dilution, a 1:2 to about a 1:10, or about 1:4 to about a 1:6 dilution. The diluted formulation can then be added dropwise to a fraction cell containing water as a dispersant for measuring. In some embodiments, the RK-33 can be milled to a D50 particle size of about 0.05 μm to about 0.5 m, about 0.08 μm to about 0.3 μm, or about 0.1 μm to about 0.1 μm. In some embodiments, the RK-33 can be milled to a D90 particle size of about 0.05 μm to about 3.0 μm, about 0.05 μm to about 2.0 μm about 0.05 μm to about 1.0 μm, about 0.1 μm to about 0.5 μm, or about 0.15 μm to about 0.3 μm. In some embodiments, the particles in the suspension have an average particle size of about 0.01 μm to about 1 μm, about 0.05 μm to about 0.50 μm, or about 0.10 μm to about 0.30 μm.

The milled particles comprising RK-33 can be placed in the formulation. Alternatively, one or more excipients and/or coatings can be added to the RK-33 particles before addition to the formulation. In some embodiments, the D50 particle size of the particles comprising RK-33 in the aqueous suspension is about 0.05 μm to about 0.5 μm, about 0.08 μm to about 0.3 μm, about 0.1 μm to about 0.1 μm. In some embodiments, the D90 particle size of the particles comprising RK-33 in the aqueous suspension is about 0.05 μm to about 3.0 μm, about 0.05 μm to about 2.0 m, about 0.05 μm to about 1.0 μm, about 0.1 μm to about 0.5 μm or about 0.15 μm to about 0.3 m. In some embodiments, the average particle size of the particles comprising RK-33 in the aqueous suspension has an average particle size of about 0.01 μm to about 1 μm, about 0.05 μm to about 0.5 μm, or about 0.10 μm to about 0.2 μm. In some embodiments, the D100 particle size is less than 5 μm, less than 4 μm, less than 3 μm, or less than 2 μm.

The disclosure provides for formulations in which the particle size does not significantly change over time. In some embodiments, stable particle size provides for increased physical stability and/or chemical stability of the formulation. In some embodiments, the stable particle size indicates no aggregation or the particles. In some embodiments, the stable particle size results in no change in viscosity over time. In some embodiments, stable particle size provides for a consistent pharmacokinetic profile when the formulation is administered to a subject. In some embodiments, the average particle size in the suspension does not change by more than 25%, more than 20%, more than 15%, more than 10% or more than 5% after storage at room temperature for two weeks, 1 month, or 6 months. In some embodiments, the average particle size in the suspension does not change by more than 20% after storage at room temperature for two weeks. In some embodiments, the average particle size in the suspension does not change by more than 20% after storage at room temperature for three months. In some embodiments, the average particle size in the suspension does not change by more than 20% after storage at room temperature for six months.

In some embodiments, the disclosure provides a liquid formulation comprising RK-33, sodium deoxycholate, PVP, and water. In some embodiments, the disclosure provides a liquid formulation comprising about 10% to about 25% (wt/wt) RK-33. In some embodiments, the disclosure provides a liquid formulation comprising about 10% to about 25% (wt/wt) RK-33, and about 0.1% to about 1.0% (wt/wt) sodium deoxycholate. In some embodiments, the disclosure provides a liquid formulation comprising about 10% to about 25% (wt/wt) RK-33, about 0.1% to about 1.0% (wt/wt) sodium deoxycholate, and about 1% to about 10% PVP. In some embodiments, the disclosure provides a liquid formulation comprising about 10% to about 25% (wt/wt) RK-33, about 0.1% to about 1.0% (wt/wt) sodium deoxycholate, and about 1% to about 10% PVP, and water.

In some embodiments, the disclosure provides a liquid formulation comprising about 10% to about 25% (wt/wt) RK-33, about 0.1% to about 1.0% (wt/wt) sodium deoxycholate, and about 1% to about 10% PVP, wherein the formulation is an aqueous suspension, and wherein the suspension comprises particles comprising RK-33. In some embodiments, the disclosure provides a liquid formulation comprising about 10% to about 25% (wt/wt) RK-33, about 0.1% to about 1.0% (wt/wt) sodium deoxycholate, and about 1% to about 10% PVP, wherein the formulation is an aqueous suspension, and wherein the suspension comprises particles comprising RK-33, wherein the D50 particle size is about 0.05 μm to about 0.5 μm.

In some embodiments, the formulations of the present disclosure are diluted in a pharmaceutically acceptable diluent, e.g., water, saline, or the like, to form a diluted formulation prior to administration. In some embodiments, the diluted formulation is stable chemically and physically for at least 1 hours, at least 2 hours, at least 6 hours, at least 12 hours or at least 24 hours. In some embodiments, the RK-33 in the diluted formulation does not precipitate (as determined, e.g., by visual inspection) for at least 1 hours, at least 2 hours, at least 6 hours, at least 12 hours or at least 24 hours. In some embodiments, the formulations of the present disclosure are diluted into an isotonic solution. Thus, the present disclosure is additionally directed to the diluted formulations of the present invention, wherein the diluted formulations are pharmaceutically acceptable and/or suitable for intravenous delivery. In some embodiments, the formulations of the present disclosure are diluted about 1:2, to about 1:1000, about 1:3 to about 1:800, about 1:5 to about 1:600, about 1:20 to about 1:60 or about 1:50: about 1:600 to provide a diluted formulation. In some embodiments, the concentration of RK-33 in the diluted formulation can be about 1 μg/mL to about 15 mg/mL, about 5 μg/mL to about 10 mg/mL, about 25 μg/mL to about 5 mg/mL, or about 100 μg/mL to about 1 mg/mL.

In some embodiments, the formulations described herein are suitable for administration to a subject, e.g., a human subject. Thus, in some embodiments, the formulations are pharmaceutically acceptable. In some embodiments, the formulation is sterile. In some embodiments, the formulation is sterilized before administration to a subject. In some embodiments, the formulation has a pH of about 4 to about 8, about 5 to about 7.5 or about 5.5 to about 7.5. In some embodiments, the formulation is isotonic. In some embodiments, the formulation is diluted into a solution prior to administration to form an intravenous solution, wherein the intravenous solution is sterile, isotonic, pharmaceutically acceptable, and/or has a pH of about 4 to about 8, about 5 to about 7.5 or about 5.5 to about 7.5.

In some embodiments, the diluted formulations are pharmaceutically acceptable. In some embodiments, the diluted formulation is sterile. In some embodiments, the diluted formulation is sterilized before administration to a subject. In some embodiments, the diluted formulation has a pH of about 4 to about 8, about 5 to about 7.5 or about 5.5 to about 7.5. In some embodiments, the diluted formulation is isotonic. In some embodiments, the diluted formulation is suitable for intravenous delivery, wherein the diluted formulation is sterile, isotonic, pharmaceutically acceptable, and/or has a pH of about 4 to about 8, about 5 to about 7.5 or about 5.5 to about 7.5.

In some embodiments, the formulations of the disclosure are sterile. The formulations of the disclosure can be sterilized by conventional, well-known sterilization techniques, including, for example, sterile filtration via bacterial-retaining filters or radiation. In some embodiments, the formulation is filter sterilized with a presterilized 0.22-micron filter. In some embodiments, the formulation is sterilized with gamma irradiation or electron-beam irradiation. In some embodiments, the formulation is sterilized with exposure to radiation levels of about 5 kilograys to about 60 kilograys, about 10 kilograys to about 50 kilograys, about 10 kilograys to about 40 kilograys, or about 15 kilograys to about 35 kilograys. In some embodiments, the formulation is sterilized with exposure to radiation levels of about 15 kilograys. In some embodiments, the formulation is sterilized with exposure to radiation levels of about 35 kilograys.

In some embodiments, the resulting sterilized formulation can be packaged for use as it is and stored, e.g., until it is administered to a subject. In some embodiments, the sterilized formulation is stable for an extended period of time before administration to a subject. In some embodiments, the sterilized formulation is stable for 1 week to 2 years. In some embodiments, the sterilized formulation is stable for 2 weeks to 1 year. In some embodiments, the sterilized formulation is stable for 3 weeks to 6 months. In some embodiments, the sterilized formulation is stable for 1 month to 6 months. In some embodiments, the sterilized formulation is stable for at least 1 month, at least 2 months, at least 3 months, at least 4 months, at least 5 months, at least 6 months, at least 7 months, at least 8 months, at least 9 months or at least 12 months. In some embodiments, stability is determined when stored at standard conditions, i.e., ambient temperature, or at reduced temperature, i.e., at 5° C.

In some embodiments, the disclosure provides that the formulations described herein can be combined with one or more additional active agents, e.g., a sedative, an analgesic, or a second chemotherapeutic agent. In some embodiments, the disclosure provides a formulation as described herein and a second chemotherapeutic agent. In some embodiments, the second chemotherapeutic agent is diluted in the same pharmaceutically acceptable diluent as the formulations of the present disclosure. Thus, in some embodiments, the disclosure provides a diluted formulation comprising the formulations disclosed herein and a second chemotherapeutic agent.

The formulations described herein can be provided by various methods. In some embodiments, the disclosure provides a method of making a liquid formulation comprising RK-33, the method comprising: (a) combining the RK-33, cholic acid or derivative thereof, a water-soluble polyvinyl polymer, and water to form a mixture; and (b) milling the mixture, wherein the method results in an aqueous suspension comprising particles. In some embodiments, the disclosure provides a method of making a liquid formulation wherein the RK-33 is milled before being combined with the cholic acid or derivative thereof, water soluble polyvinyl polymer and/or water. Thus, in some embodiments, the formulations are made by a method comprising (a) milling RK-33, and (b) combining the milled RK-33 to cholic acid or derivative thereof, water soluble polyvinyl polymer and/or water, wherein the method results in an aqueous suspension comprising particles.

Various means of making particles of an active agent of a desired size are known in the art, and are envisioned by the present disclosure to achieve the desired particle size. In some embodiments, the means for reducing particle size is continued until the desired particle size is achieved. In some embodiments, the desired particle size is isolated using a sieve. In some embodiments, the particle size is achieved using a mill, e.g., dry milling or wet milling, a chopper, a pulverizer, a hammer mill, or an air classifying mill. In some embodiments, the milling is performed using a vibratory ball mill. Efficacy and efficiency of the vibratory ball mill can be adjusted by using various speeds of the mills. In some embodiments, the formulation is milled using a vibratory ball mill at about 1,000 RPM to about 10,000 RPM, or about 2,000 RPM to about 4,000 RPM. In some embodiments, the formulation is milled using a vibratory ball mill for at least 10 minutes, for about 5 minutes to about 5 hours, or for about 20 minutes to about 60 minutes. In some embodiments, the formulation is milled using a vibratory ball mill at about 2,000 RPM to about 4,000 RPM for about 20 minutes to about 60 minutes.

In some embodiments, the RK-33, cholic acid or derivative thereof, water soluble polyvinyl polymer and/or water are mixed using mixer, e.g., a microfluidizer, to form a suspension. In some embodiments, the RK-33, cholic acid or derivative thereof, water soluble polyvinyl polymer and/or water are mixed multiple times using a mixer, e.g., 1 to 20 passes using a microfluidizer. The number of passes, the pressure used by the microfluidizer and the duration of the mixing can be adjusted until the particles are completely suspended without aggregates.

The formulations of the present disclosure can be used for the treatment of cancer. In some embodiments, the formulations of the present invention are diluted in a pharmaceutically acceptable diluent, e.g., water, saline, e.g., an isotonic saline solution, Ringers lactate solution, Dextrose 5 in 0.9% sodium chloride, or the like, and then administered to a subject. In some embodiments, the formulations of the present disclosure are diluted into an isotonic solution, and then administered intravenously to a subject. Thus, in some embodiments, the method of treating a cancer in a subject comprises (a) diluting the formulation as described herein to form a diluted formulation, and (b) intravenously administering to the subject the diluted formulation. In some embodiments, the formulations described herein can be administered directly to the subject for the treatment of cancer.

In some embodiments, the formulations and methods provided herein provide an improved delivery method of RK-33 into the subject in need thereof, e.g., a subject being treated for cancer. In some embodiments, the improved mode of administering increases the efficiency and/or efficacy of radiation treatment. In some embodiments, the method of treating cancer in a subject further comprises subjecting the subject to focused radiation. In some methods, the focused radiation is stereotactic ablative radiotherapy (SABR).

Various dosing frequencies can be used according to the present disclosure in the methods of treating cancer in a subject. In some embodiments, the formulation is administered to the subject about 10 minutes to about 1 week, about 30 minutes to about 3 days, about 1 hour to about 1 day, or about 2 hours to about 12 hours before the focused radiation. In some embodiments, the formulation is administered one to ten times, about 1 to about 5 times, about 1 to about 3 times, about 2 to about 5 times, about 3 to about 5 times before the focused radiation.

In some embodiments, the methods of treating cancer using the formulations as described herein can comprise administering a second chemotherapeutic agent in conjunction with the described formulations. In some embodiments, the second chemotherapeutic agent is administered simultaneously with the formulations described herein. For example, in some instances the disclosed formulation and the chemotherapeutic agent can both be diluted in the same pharmaceutically acceptable diluent. In a separate embodiment, the disclosure provides a method of treating cancer by first administering RK-33 using the formulations described herein, and then administering a second chemotherapeutic agent. In a further embodiment, the disclosure provides a method of treating cancer by first administering a second chemotherapeutic agent, and then administering RK-33 using the formulations described herein.

In some embodiments, the method of treating cancer is a subject comprises administering the formulations described herein multiple times. In some embodiments, the method of treating cancer in a subject comprises administering the formulations greater than 2 times, greater than 3 times, greater than 4 times, greater than 5 times, greater than 6 times, greater than 7 times, greater than 8 times or greater than 9 times. In some embodiments, the method is repeated two to 20 times. In some embodiments, the administering continues until the symptoms associated with the cancer are substantially eliminated.

Various cancers can be treating according to the present disclosure. In some embodiments, the cancer is lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, chronic or acute leukemia, lymphocytic lymphomas, cancer of the bladder, cancer of the kidney, renal cell carcinoma, neoplasms of the central nervous system (CNS), neuroectodermal cancer, spinal axis tumors, glioma, meningioma, and pituitary adenoma.

In some embodiments, the disclosure provides a kit comprising the formulations of the present disclosure. In some embodiments, disclosure provides a kit comprising the formulations of the present disclosure and a packaging suitable for storing the formulation, e.g., until it is used. In some embodiments, the packaging is a vial, a pre-filled syringe or an IV bag. In some embodiments, the packaging is vial, e.g., a glass vial. In some embodiments, the packaging is a vial with a rubber stopper. In some embodiments, the kit comprises a packaging comprising the formulations described herein, and a packaging comprising a pharmaceutically acceptable diluent. In some embodiments, the kit comprises a means for transferring the formulations described herein to the pharmaceutically acceptable diluent. In some embodiments, the kit comprises two or more packages comprising the formulations described herein, e.g., two or more vials, e.g., three, four, five, six, seven, eight or nine packages, e.g., vials. In some embodiments, the kit comprises a package with an amount of RK-33 sufficient for a single administration. In some embodiments, the kit comprises multiple packages, each package comprising the formulation with an amount of RK-33 sufficient for a single administration. In some embodiments, the number of packages is sufficient for one series of a dosage regimen.

All references cited herein, including patents, patent applications, papers, textbooks and the like, and the references cited therein, to the extent that they are not already, are hereby incorporated herein by reference in their entirety.

EXAMPLES

Example 1—Analysis of Solubility of RK-33 in Various Solvents

The degree of solubility of RK-33 in various solubilizers were tested. RK-33 was added to the solubilizer and observed for formation of homogenous molecular dispersion and physical appearance. The qualitative solubility and physical appearances of the solutions are shown in Table 1.

TABLE 1

| Solvent | Qualitative Solubility (mg/mL) | Observation |
|---|---|---|
| DMA | >100 | Clear, yellow colored solution |
| DMSO | >100 | Clear, yellow colored solution |

TABLE 1-continued

| Solvent | Qualitative Solubility (mg/mL) | Observation |
|---|---|---|
| NMP | >100 | Clear, yellow colored solution |
| PEG 200 | ~12 | Clear, yellow colored solution |
| PEG300 | ~10 | Clear, yellow colored solution |
| PEG 400 | >5 to <10 | Clear, yellow colored solution |
| PG | >1 to <5 | Clear, yellow colored solution |
| Water | <1 | Poor wettability |
| Water (pH 1.6) | <1 | Poor wettability |
| Water (pH 4) | <1 | Poor wettability |
| Water (pH 8) | <1 | Poor wettability |
| Water (pH 10) | <1 | Poor wettability |
| Ethanol | <1 | Yellow dispersion |
| Glycerin | <1 | Dispersion |
| Miglyol 810 | <1 | Dispersion |
| Olive oil | <1 | Dispersion |
| Oleic acid | <1 | Dispersion |
| Corn oil | <1 | Dispersion |
| Labrafil 1944CS | <1 | Dispersion |
| Gelucire 44/14 | <1 | Dispersion |
| Glycerol formal | >75 | Clear, yellow colored solution |
| Benzyl alcohol | >250 | Clear, yellow colored solution |

Example 2—Development of Stable RK-33 Liquid Formulations

RK-33 formulations comprising of various combinations of solvents and polymers were prepared and analyzed for color, visual precipitation and clarity. Results as observed are outlined in Table 2, Table 3 and Table 4.

TABLE 2

| | Trial | | | | | | | |
|---|---|---|---|---|---|---|---|---|
| Composition | T1 | T2 | T3 | T4 | T5 | T6 | T7 | T8 |
| RK-33 | 5 mg | 5 mg | 5 mg | 5 mg | 5 mg | 5 mg | 5 mg | 5 mg |
| NMP | — | — | — | — | — | — | — | — |
| DMA | — | — | — | — | — | — | — | — |
| PEG 200 | — | — | — | — | — | — | 30% v/v | 30% v/v |
| PEG 400 | 50% v/v | 50% v/v | 50% v/v | 50% v/v | 50% v/v | 50% v/v | 10% v/v | 10% v/v |
| PG | — | — | | | | | | |
| HPβCD | — | — | 4% w/v | 4% w/v | — | 4% w/v | — | 4% w/v |
| poloxamer 188 | — | 5% w/v | — | — | — | — | — | — |
| HPMC 6 cps | | | | | | | — | — |
| pH adjustment | — | — | — | to pH 4 with 0.1N HCl | to pH 4 with 0.1N NaOH | — | — | — |
| Purified water | 50% v/v (or) | q.s to 1 ml | q.s to 1 ml | q.s to 1 ml | q.s to 1 ml | — | q.s to 1 mL | q.s to 1 mL |
| Normal saline | — | — | — | — | — | q.s to 1 ml | — | — |
| Mannitol | — | — | — | — | — | — | — | — |
| PBS pH 7.4 | 50% v/v | — | — | — | — | — | — | — |
| Formulation | not clear | not clear | clear | not clear | not clear | not clear | not clear | not clear |
| PBS dilution test (1:9) | — | — | Initially colloidal, within 2-5 minutes curdy ppt. | — | — | — | — | — |

TABLE 3

| | Trial | | | | | | | |
|---|---|---|---|---|---|---|---|---|
| Composition | T9 | T10 | T11 | T12 | T13 | T14 | T15 | T16 |
| RK-33 | 5 mg | 5 mg | 5 mg | 5 mg | 2.5 mg | 2.5 mg | 2.5 mg | 2.5 mg |
| NMP | — | — | — | — | — | — | — | — |
| DMA | — | — | — | — | — | — | — | — |
| PEG 200 | 25% v/v | 30% v/v | 30% v/v | 30% v/v | — | 30% v/v | 30% v/v | 25% v/v |
| PEG 400 | 25% v/v | — | 10% v/v | 10% v/v | 50% v/v | 10% v/v | 10% v/v | 25% v/v |
| PG | | 20% v/v | — | — | | — | — | — |
| HPβCD | 4% w/v | 4% w/v | 4% w/v | 4% w/v | 4% w/v | — | 4% w/v | 4% w/v |
| poloxamer 188 | — | — | — | — | — | — | — | — |
| HPMC 6 cps | — | — | — | 0.5% w/v | | — | — | — |
| pH adjustment | — | — | — | — | — | — | — | — |
| Purified water | q.s to 1 mL | q.s to 1 mL | | q.s to 1 mL | q.s to 1 ml | — | q.s to 1 mL | q.s to 1 mL |
| Normal saline | — | — | — | — | — | — | — | — |
| Mannitol | — | — | q.s to 1 mL with 5% w/v mannitol | — | — | q.s to 1 mL with 5% w/v mannitol | — | — |
| Observation | T9 | T10 | T11 | T12 | T13 | T14 | T15 | T16 |
| Formulation | not clear | not clear | not clear | not clear | clear | not clear | not clear | clear |
| PBS dilution test (1:9) | — | — | — | — | Initial-colloidal 5 min - colloidal | — | — | Initial-colloidal 5 min - colloidal |

TABLE 4

| | Trial | | | | | |
|---|---|---|---|---|---|---|
| Composition | T17 | T18 | T19 | T20 | T21 | T22 |
| RK-33 | 5 mg | 5 mg | 5 mg | 5 mg | 5 mg | 5 mg |
| Benzyl alcohol | — | — | — | — | — | — |
| NMP | — | — | — | — | 5% v/v | 5% v/v |
| DMA | — | 2% v/v | — | 5% v/v | — | — |
| PEG 200 | 25% v/v | 25% v/v | 25% v/v | — | — | 30% v/v |
| PEG 300 | | | | | | |
| PEG 400 | 25% v/v | 25% v/v | 25% v/v | — | — | — |
| HPβCD | 4% w/v | 4% w/v | 4% w/v | 4% w/v | 4% w/v | 4% w/v |
| solutol HS15 | — | — | — | — | — | — |
| poloxamer 188 | — | — | — | — | — | — |
| HPMC 6 cps | 0.5% w/v | — | — | — | — | — |
| sorbitol | — | — | — | — | — | — |
| Purified water | q.s to 1 mL | q.s to 1 mL | q.s to 1 mL | q.s to 1 mL | q.s to 1 mL | q.s to 1 mL |
| Normal saline | — | — | — | — | — | — |
| Mannitol | — | — | 5% w/v | — | — | — |
| PBS pH 7.4 | — | — | — | — | — | — |
| Formulation | | precipitated when cosolvents added to organic solvent | not clear | not clear | not clear | not clear |

| | Trial | | | | |
|---|---|---|---|---|---|
| Composition | T23 | T24 | T25 | T26 | T27 |
| RK-33 | 5 mg | 5 mg | 5 mg | 5 mg | 5 mg |
| Benzyl alcohol | — | — | — | — | — |
| NMP | — | 5% v/v | 5% v/v | 5% v/v | 5% v/v |
| DMA | — | — | — | — | — |
| PEG 200 | 25% v/v | 25% v/v | 25% v/v | 25% v/v | 25% v/v |
| PEG 300 | | | | 25% v/v | 25% v/v |
| PEG 400 | 25% v/v | 25% v/v | 25% v/v | — | — |
| HPβCD | — | 5% w/v | — | 5% w/v | 5% w/v |
| solutol HS15 | — | | 5% w/v | — | 5% w/v |
| poloxamer 188 | — | — | — | — | — |
| HPMC 6 cps | — | — | — | — | — |
| sorbitol | 5% w/v | — | — | — | — |

TABLE 4-continued

| | | | | | |
|---|---|---|---|---|---|
| Purified water | q.s to 1 mL | q.s to 1 mL | q.s to 1 mL | q.s to 1 mL | q.s to 1 mL |
| Normal saline | — | — | — | | |
| Mannitol | — | — | — | | |
| PBS pH 7.4 | — | — | — | | |
| Formulation | not clear | not clear | Initially clear, but precipitated in 1 min | not clear | not clear |

As shown above, there was significant precipitation and discoloration observed in the initial intravenous formulations comprising RK-33 with the listed polymers and solvents.

Formulations comprising of various combinations of solvents and polymers were prepared with an intralipid emulsion used to provide calories to patients who receive an injection into the vein. The prepared formulations were then analyzed for color, visual precipitation and clarity. Results as observed are outlined in Table 5.

TABLE 5

| | Trial | | | | | |
|---|---|---|---|---|---|---|
| Composition | T28 | T29 | T31 | T32 | T38 | T39 |
| RK-33 | 10 mg | 10 mg | 10 mg | 10 mg | 5 mg | 2.5 mg |
| Benzyl alcohol | — | — | — | — | 2% v/v | 2% v/v |
| NMP | — | 5% v/v | — | — | — | — |
| DMA | 10% v/v | — | — | — | — | — |
| PEG 200 | — | — | 50% v/v | — | 30% v/v | 30% v/v |
| PEG 300 | — | — | — | 50% v/v | — | — |
| Intralipid | q.s to 1 mL | q.s to 1 mL | q.s to 1 mL | q.s to 1 mL | q.s to 1 mL | q.s to 1 mL |
| Formulation | precipitated | precipitated | precipitated | precipitated | precipitated | precipitated, emulsion broken |

Each of the formulations in Table 5 comprising intralipid precipitated.

Formulations comprising of various combinations of solvents and polymers, including Captisol®, were prepared. The formulations were analyzed for color, visual precipitation and clarity. Results are presented in Table 6.

TABLE 6

| | | | | | Captisol Trials | |
|---|---|---|---|---|---|---|
| Composition | T30 | T33 | T34 | T35 | T36 | T37 |
| RK-33 | 5 mg | 5 mg | 5 mg | 5 mg | 5 mg | 5 mg |
| Benzyl alcohol | — | — | — | — | — | — |
| NMP | 5% v/v | 5% v/v | 5% v/v | 5% v/v | — | — |
| DMA | — | — | — | — | — | — |
| PEG 200 | 25% v/v | 50% v/v | 25% v/v | — | 25% v/v | 50% v/v |
| PEG 300 | 25% v/v | — | | — | — | — |
| PEG 400 | — | — | 25% v/v | 40% v/v | 25% v/v | — |
| PG | q.s to 1 mL with 40% w/v HPBCD | — | — | — | — | — |
| Captisol | — | — | — | — | 5% w/v Captisol | 5% w/v Captisol |
| HPβCD | — | — | 11% w/v added up to 1 mL | 5% w/v (q.s. of 10% w/v solution added to 1 mL) | — | — |

TABLE 6-continued

| Composition | T30 | T33 | T34 | T35 | T36 | T37 |
|---|---|---|---|---|---|---|
| | | | | | Captisol Trials | |
| Solutol HS15 | — | 5% w/v | — | — | — | — |
| Purified water | — | q.s to 1 mL | | — | q.s to 1 mL | q.s to 1 mL |
| Formulation | not clear | not clear | Initially clear, but precipitated in 1 min | not clear | not clear | not clear |

RK-33 formulation (2.5 mg/mL) was achieved with 50% PEG 200 and 4% HPβCD. Cyclodextrins were not useful to achieve higher solution concentrations of RK-33. Even solvents such as glycerol and benzyl alcohol did not help in achieving a formulation comprising RK-33 of at least 2.5 mg/mL.

Various additional pharmaceutical formulations were tested in an attempt to increase the concentration of RK-33 to 20% (w/w) as outlined in Table 7.

TABLE 7

| Formulation | RK-33 % (w/w) | PVP K-12 % (w/w) | PS-20 % (w/w) | Sodium Deoxycholate % (w/w) | Poloxamer 188 | Sodium carboxymethyl cellulose 7L2P |
|---|---|---|---|---|---|---|
| T38 | 20 | — | 4.0 | — | — | — |
| T39 | 20 | 4.0 | 2.0 | — | — | — |
| T40 | 20 | 4.0 | — | 0.4 | — | — |
| T41 | 20 | — | — | — | 4.0 | — |
| T42 | 20 | — | 2.0 | — | — | 4.0 |
| T43 | 20 | — | — | — | 5.0 | — |

No visible precipitates were observed for any of Formulations T38-T43. The particle size distribution (PSD) of Formulations T41, T42 and T43 after periods of milling are shown in Table 8.

TABLE 8

| Formulation | Milling Duration | PSD D90 (μm) | PSD Median (μm) | PSD Mean (μm) |
|---|---|---|---|---|
| T41 | 30 min | 16.33 | 10.40 | 10.88 |
| T42 | 30 min | 1.61 | 0.21 | 0.81 |
| T43 | 45 min | 13.97 | 9.25 | 9.66 |

Figure 1B:
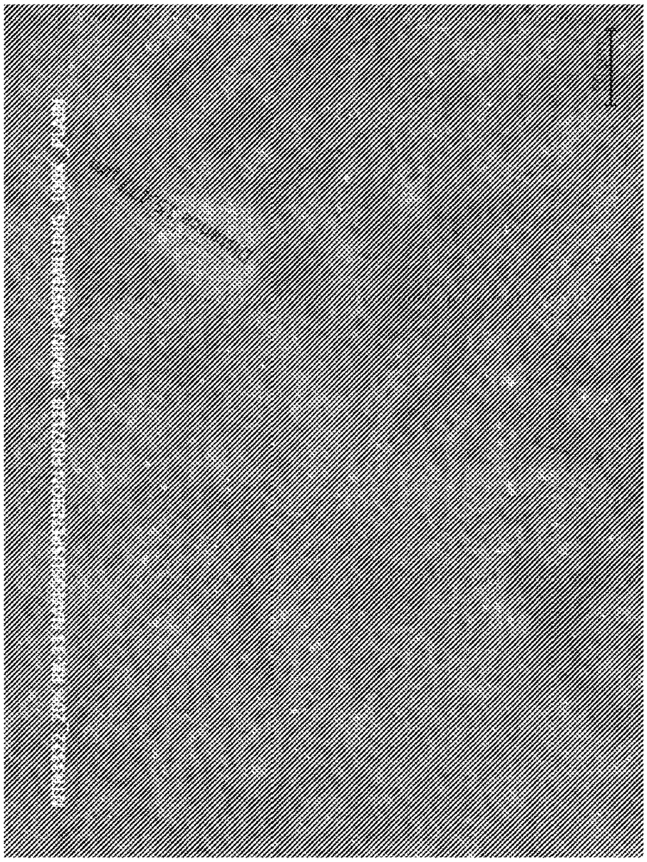
FIG. 1B is a photo of particle aggregation of Formulation T42 observed under the microscope.

As noted in Table 8, Formulations T41 and T42 were milled for 30 minutes at 3000 RPM. Following milling, particle aggregation of Formulations T41 and T42 was observed under the microscope and in particle size distribution (PSD). Initial observations in preparation of samples included an increase in viscosity and difficulty in extracting the suspension from the formulations. The particle aggregation of Formulations T41 and T42 as observed under the microscope can be seen in FIG. 1A and FIG. 1B, respectively.

Figure 2B:
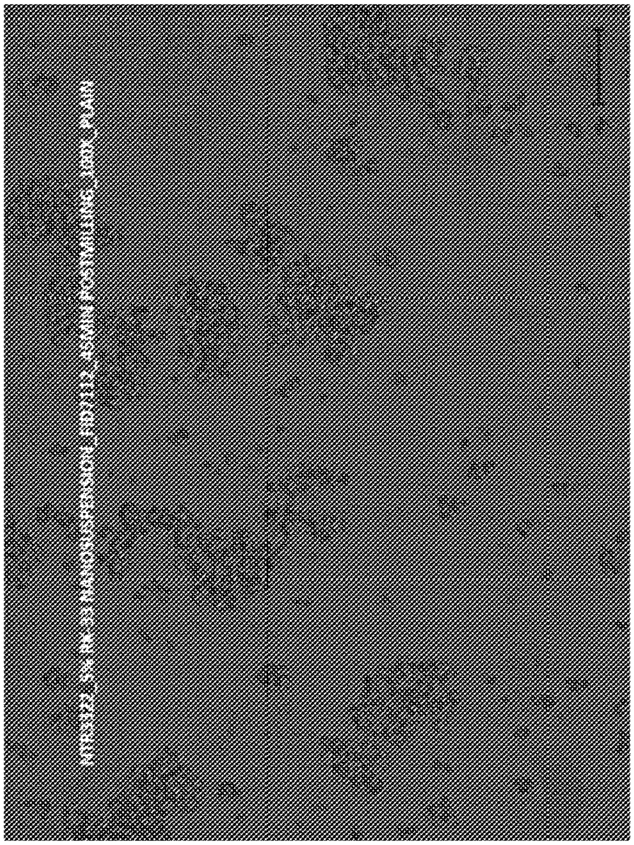
FIG. 2B is a photo of particle aggregation of Formulation T43 under microscope after an additional 15 minutes of milling (45 minutes total).
Figure 2A:
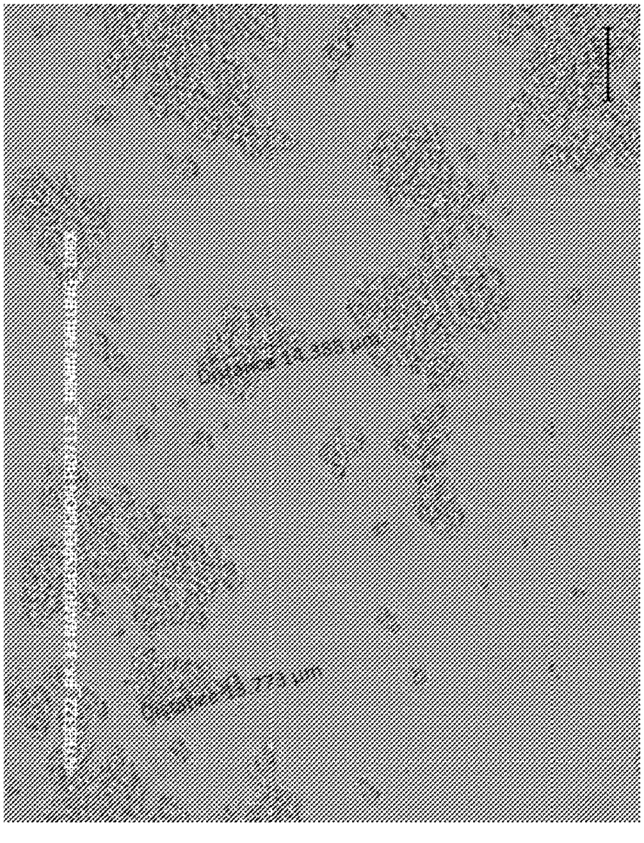
FIG. 2A is a photo of particle aggregation of Formulation T43 under microscope after 30 minutes of milling.

Formulation T43 was first milled at 3000 RPM for 30 minutes and then analyzed for particle aggregation. Particle aggregation was observed. Formulation T43 was further milled for another 15 minutes at the same speed. No reduction in particle aggregation was observed by the additional milling. The particle aggregation of T43 30 minutes milling and T43 45 minutes milling as observed under the microscope can be seen in FIG. 2A and FIG. 2B, respectively.

Formulation T40 (20% w/w RK-33, 0.4% w/w Sodium deoxycholate, 4% w/w PVP K12) was milled for 30 minutes using a high energy benchtop mill, and then stored at ambient or in 5° C. conditions for up to two weeks. To prepare a sample of Formulation T40 for particle size determination measurements, the formulation was diluted with deionized water and then added dropwise to a fraction cell containing water as a dispersant. The particle size distributions of Formulation T40 stored at either ambient temperature or at 5° C. for $T_0$, $T_1$=1 week or $T_2$=2 weeks was determined. Results are outlined in Table 9.

TABLE 9

Formulation T40

| Time Point | Storage Conditions | D90 (μm) | Median (μm) | Mean (μm) |
|---|---|---|---|---|
| $T_0$ | — | 0.20 | 0.14 | 0.14 |
| $T_1$ | Ambient | 0.22 | 0.15 | 0.15 |
| $T_1$ | 5° C. | 0.21 | 0.14 | 0.15 |
| $T_2$ | Ambient | 0.21 | 0.14 | 0.15 |
| $T_2$ | 5° C. | 0.22 | 0.15 | 0.15 |

Figure 3:
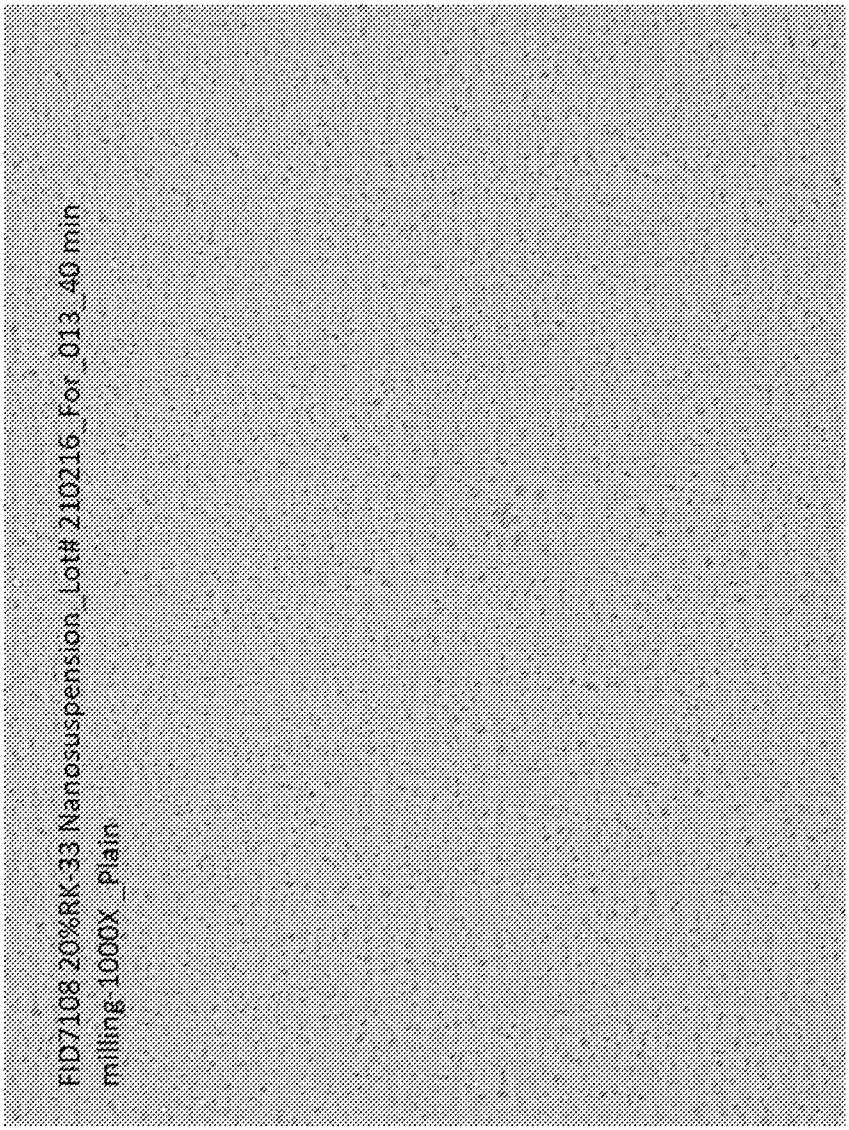
FIG. 3 is a photo of particle aggregation of Formulation T40 under microscope after 40 minutes of milling. The particles are evenly dispersed with little or no particle aggregation.

There was no significant difference between the particle size distribution aggregation of the Formulation T40 in storage condition 5° C. at $T_0$ and at $T_2$ at the end of the two-week study. As shown in FIG. 3 was evenly dispersed with little to no particle aggregation, although some small needle like particles were observed in Formulation T40 in optical microscopy. Based on these results, Formulation T40 is considered to be the most stable intravenous suspension formulation of RK-33.

What is claimed is:

1. A liquid formulation comprising, a. RK-33 as represented by Formula I

Formula I

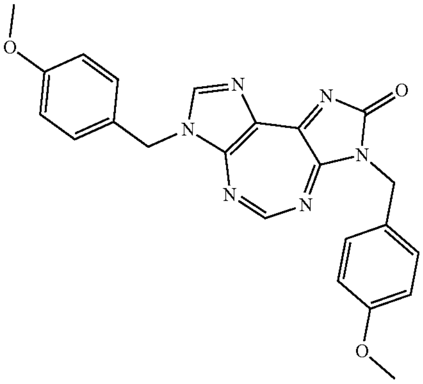

b. cholic acid or derivative thereof, c. a water-soluble polyvinyl polymer, and d. water, wherein the RK-33 does not precipitate or significantly aggregate.

2. The liquid formulation of claim 1, wherein the formulation comprises about 1 mg/mL to about 30 mg/mL of RK-33.

3. The liquid formulation of claim 1, wherein the cholic acid or derivative thereof is sodium deoxycholate.

4. The liquid formulation of claim 1, wherein the formulation comprises about 0.05% w/w to about 1.0% w/w cholic acid or derivative thereof.

5. The liquid formulation of claim 1, wherein the water-soluble polyvinyl polymer is polyvinylpyrrolidone (PVP), polyvinyl alcohol (PVOH), polyvinyl alcohol-polyethylene glycol copolymer, or polyvinylpyrrolidone-polyvinyl acetate (PVP-VA).

6. The liquid formulation of claim 1, wherein the polyvinylpyrrolidone has an average molecular weight of about 1000 Da to about 20,000 Da.

7. The liquid formulation of claim 1, wherein particles in the formulation have a D50 particle size of about 0.05 μm to about 0.5 μm.

8. The liquid formulation of claim 1, wherein the average particle size in the formulation does not change by more than 25% after storage at room temperature for two weeks.

9. The liquid formulation of claim 1, wherein the formulation is isotonic.

10. The liquid formulation of claim 1, wherein the formulation further comprises another chemotherapeutic agent.

11. A liquid formulation comprising, a. about 10% to about 25% (wt/wt) RK-33;

b. about 0.1% to about 1.0% (wt/wt) sodium deoxycholate;

c. about 1% to about 10% PVP; and e. water, wherein the RK-33 does not precipitate or significantly aggregate.

12. The liquid formulation of claim 1, wherein particles in the formulation have a D90 particle size of about 0.05 μm to about 0.5 μm.

13. The liquid formulation of claim 1, wherein particles in the formulation do not precipitate after storage at room temperature for greater than 2 weeks.

14. A kit comprising the formulation of claim 1 and a packaging suitable for storing the formulation, wherein the packaging is a vial, a pre-filled syringe or an IV bag.

15. A method of treating a cancer in a subject, the method comprising (a) diluting the formulation of claim 1 to form a diluted formulation, and (b) intravenously administering to the subject the diluted formulation.

16. The method of claim 15, wherein the method further comprises subjecting the subject to focused radiation.

17. The method of claim 15, wherein the formulation is administered to the subject about 10 minutes to about 1 week before the focused radiation.

18. The method of claim 15, wherein the formulation is administered one to ten times before the focused radiation.

19. The method of claim 15, wherein the cancer is lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual or reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, chronic or acute leukemia, lymphocytic lymphomas, cancer of the bladder, cancer of the kidney, renal cell carcinoma, neoplasms of the central nervous system (CNS), neuroectodermal cancer, spinal axis tumors, glioma, meningioma, and pituitary adenoma.

* * * * *